US006197805B1

(12) United States Patent
Smith

(10) Patent No.: US 6,197,805 B1
(45) Date of Patent: Mar. 6, 2001

(54) BROAD SPECTRUM ANTIMICROBIAL MIXTURES

(75) Inventor: Roger Errol Smith, Neshanic Station, NJ (US)

(73) Assignee: Troy Technology Corporation, Inc., Wilmington, DE (US)

( * ) Notice: Subject to any disclaimer, the term of this patent is extended or adjusted under 35 U.S.C. 154(b) by 0 days.

(21) Appl. No.: 09/321,022

(22) Filed: May 27, 1999

(51) Int. Cl.$^7$ .................... A01N 43/52; A01N 43/34; A01N 43/36; A01N 42/10
(52) U.S. Cl. .................. 514/388; 504/155; 504/156; 504/159; 106/15; 514/478; 514/479; 514/484; 514/485
(58) Field of Search .................. 514/388, 478, 514/479, 484, 485; 504/155, 156, 159; 106/15

(56) References Cited

U.S. PATENT DOCUMENTS

| 3,923,870 | 12/1975 | Singer ................. 260/482 C |
| 4,259,350 | 3/1981 | Morisawa et al. ............ 424/408 |
| 4,592,773 | 6/1986 | Tanaka et al. ............... 71/88 |
| 4,616,004 | 10/1986 | Edwards ..................... 514/63 |
| 4,719,227 | 1/1988 | Shade et al. ................ 514/452 |
| 4,945,109 | 7/1990 | Rayudu ...................... 514/478 |

FOREIGN PATENT DOCUMENTS

| 197 05 085A1 | 6/1998 | (DE) . |
| 289317 A1 | 11/1988 | (EP) . |
| 458060 A1 | 11/1991 | (EP) . |
| 562164 A1 | 9/1993 | (EP) . |
| 2164803 | 6/1990 | (JP) . |
| 4051959 | 2/1992 | (JP) . |
| 5112739 | 5/1993 | (JP) . |
| 06313269 | 11/1994 | (JP) . |
| 07148498 A2 | 6/1995 | (JP) . |
| 9067797 | 3/1997 | (JP) . |

OTHER PUBLICATIONS

Tomlin, Clive, "Carbendazim," The Pesticide Manual, 10th ed., Crop Protection Publications (Surrey in UK), vol. ? (No. ?), p. 150 & 151, (Oct. 2, 1994).

Primary Examiner—Allen J. Robinson
(74) Attorney, Agent, or Firm—Robert F. Tavares

(57) ABSTRACT

This invention is directed to a broad spectrum antimicrobial composition which comprises a mixture of an iodopropynyl compound in combination with 2-(methoxycarbonylamino) benzimidazole and, where desirable, an algicide said mixture provided in an amount sufficient to protect a substrate from attack by one or more organisms. The composition can be used broadly in industrial systems and more particularly with substrates such as paints, coatings, stucco, concrete, stone, cementaceous surfaces, wood, caulking, sealants, textiles, leather, wood, preservatives, metal working fluids, drilling muds, clay slurries, glazes, optical brightness, carpet backing, pigments and as a preservative for other aqueous and wet state products, and the like.

19 Claims, No Drawings

BROAD SPECTRUM ANTIMICROBIAL MIXTURES

BACKGROUND OF THE INVENTION

1. Field of the Invention

The present invention pertains to broad spectrum antimicrobial compositions suitable for use in the protection of paints and paint films, wood products, leather, metal working fluids, mineral slurries, inks, dispersions and other wet state industrial products or processes from spoilage resulting from the growth of microorganisms, especially fungi and algae. The antimicrobial compositions of this invention include mixtures comprising 2-(methoxycarbonylamino) benzimidazole, an iodopropynyl compound and, where desirable, an algicide. These combinations are especially useful in protecting stucco, paint, coatings, Exterior Insulation Finish Systems (EIFS), leather, wood products, and construction materials such as tape-joint compounds, caulks, sealants, and adhesives.

2. Description of the Background

Substrates of all types and water-containing compositions and formulations, when exposed to common environmental conditions are prone to attack, spoilage and various kinds of destruction by a variety of species of microorganisms including fungi, yeast, bacteria and algae. As a result, there has always been a great need for effective and economical means to protect, for extended periods of time, commercial compositions and formulations from the deterioration and destruction caused by such microorganisms.

Materials which need protection against such microorganisms include, for example, materials such as paints and other coating formulations, surfactants, proteins, starch-based compositions, inks, emulsions and resins, stucco, concrete, stone, wood, adhesives, caulks, sealants, leather, and spin finishes. Other important commercial materials such as polymer dispersions or aqueous latex paints containing polyvinyl alcohol, polyacrylates or vinylpolymers, thickener solutions containing cellulose derivatives, clay and mineral suspensions and metal working fluids, also are prone to degradation by the action of objectionable microorganisms which can spoil and significantly impair the usefulness of such compositions. Such degradation may produce, inter alia, changes in pH values, gas formation, discoloration, the formation of objectionable odors, and/or changes in rheological properties.

Antimicrobials are also important during the processing of materials. For example animal skins are susceptible to attack by microorganisms both prior to and after the tanning process. Prior to the tanning process, bactericides are used in the brine solutions to prevent bacteria from damaging the hide grain. After the tanning process, the so called wet blue hides are subject to fungal attack during storage or transport and fungicides are used to inhibit this fungal growth. Antimicrobials can also be used in the fat liquors and leather finishing products to prevent the growth of bacteria, fungi and yeast.

A great deal of effort has gone into developing a wide variety of materials which, to various degrees, are effective in retarding or preventing the growth of, and accompanying destruction caused by, such microorganisms in a variety of circumstances. Such antimicrobial materials included halogenated compounds, organometallic compounds, quaternary ammonium compounds, phenolics, metallic salts, heterocyclic amines, formaldehyde adducts, organosulfur compounds and the like.

No single organic antimicrobial compound is able to provide protection against all microorganisms or is suitable for all applications. In addition to such limitations concerning efficacy, other limitations may restrict the usefulness of certain antimicrobials. For example the stability, physical properties, toxicological profile, regulatory considerations, economic considerations or environmental concerns may render a particular ingredient unsuitable for a particular use. There is a need, therefore, to constantly develop new combinations that will offer broad spectrum protection from a variety of needs.

A judicious choice of combinations may provide a way to maximize benefits while at the same time minimize problems. Ideally, a combination wherein the antimicrobial activity is enhanced while the less desirable properties are suppressed can provide a superior product. The task is to find such combinations that will provide protection against a wide variety of problem microorganisms, will not adversely affect the product to be protected, will maintain its integrity for an extended period of time, and will not have any adverse effect on health or the environment.

While some combinations of 2-(methoxcarbonylamino) benzimidazole, 3-iodo-2-propynyl-butyl carbamate and algicides have been reported, the novel combinations of this invention, combinations which demonstrate the kind of unexpected properties and activities that allow them to be used in an unanticipated way, have not been reported.

SUMMARY OF THE INVENTION

The present invention is directed to certain antimicrobial mixtures comprising an iodopropynyl compound, 2-(methoxycarbonylamino)benzimidazole (BCM) and, where desirable, an algicide wherein the ratio of the BCM to the iodopropynyl compound is greater than 2 to 1. The present invention is also directed to methods for inhibiting microbial growth which comprises using mixtures of said ingredients.

DETAILED DESCRIPTION OF THE INVENTION

It has been found that when iodopropynyl compounds such as 3-iodo-2-propynyl butyl carbamate (IPBC) are combined with 2-(methoxycarbonylamino)benzimidazole (BCM) in a ratio which is greater than about 2 parts BCM to about 1 part iodopropynyl compound, they form antimicrobial compositions which are surprisingly effective in a variety of applications.

The combinations of BCM and iodopropynyl compound of this invention offer a number of advantages in a variety of applications which are both novel and unexpected. It has been found that in the combinations of this invention, the BCM and iodopropynyl compounds complement one another in a way that could not be anticipated. The iodopropynyl compound and BCM show synergistic activity and the presence of the BCM also inhibits the tendency of the iodopropynyl compound to cause coatings to yellow. This unexpected synergistic activity in combination with the unexpected resistance to yellowing offers a number of advantages in a variety of applications.

While a ratio of about three parts BCM to about 1 part iodopropynyl compound is especially preferred, any ratio in the range of greater than 2:1 to 4:1 will be preferred while any ratio in the range of greater than 2:1 to 100:1 will be suitable.

It was found that the addition of appropriate amounts of an algicide to such BCM, halopropynyl mixtures produces an antimicrobial combination that offers broad spectrum antifungal and antialgal protection in a variety of applications including paints, coatings, leather, wood products and the like.

These antimicrobial mixtures provide a high level of activity over a prolonged period of time, providing the strengths of the individual ingredients while minimizing the weaknesses of each. It is this type of complimentary activity that allows one to use less biocide in combination to achieve a desired effect at levels that cannot be achieved with any of the individual ingredients.

The halopropynyl compounds that can be used in accordance with the present invention, for the most part, are well known and can be generally identified by the following structure:

wherein Y is halogen, and X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part, is preferably an ether, an ester, or a carbamate group. The functional group of which nitrogen is a part is preferably an amine, an amide, or a carbamate group. The functional group of which sulfur is a part is preferably a thiol, a thiane, a sulfone, or a sulfoxide group. The organic functional group of which carbon is a part is preferably an ester, a carbamate or an alkyl group.

Examples of compounds which may be used as the halopropynyl compound of this invention are especially the active iodopropynyl derivatives some of which are reported in U.S. Pat. Nos. 3,923,870; 4,259,350; 4,592,773; 4,616,004; 4,719,227; and 4,945,109. These iodopropynyl derivatives include compounds derived from propynyl or iodopropynyl alcohols such as esters, acetals, carbamates and carbonates and further include the iodopropynyl derivatives of pyrimidines, thiazolinones, tetrazoles, triazinones, sulfamides, benzothiazoles, ammonium salts, carboxamides, and ureas. The preferred and most widely used among these compounds is the halopropynyl carbamate, 3-iodo-2-propynyl butyl carbamate. These compounds are included within the useful class of compounds having the generic formula:

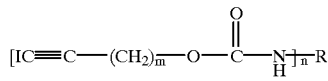

wherein R may have one to three linkages corresponding to n and is selected from the group consisting of hydrogen, substituted and unsubstituted alkyl groups having from 1 to 20 carbon atoms, substituted and unsubstituted aryl, alkylaryl, and aralkyl of from 6 to 20 carbon atoms or cycloalkyl and cycloalkenyl groups of from 3 to 10 carbon atoms, and m and n are independently integers from 1 to 3, i.e., they are not necessarily the same.

Particularly preferred are formulations of such halopropynyl carbamates where m is 1 and n is 1 and which have the following formula:

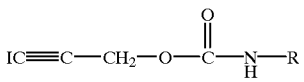

Suitable R substituents include alkyls such as methyl, ethyl, propyl, n-butyl, t-butyl, pentyl, hexyl, heptyl, octyl, nonyl, decyl, dodecyl, and octadecyl; cycloalkyls such as cyclohexyl; aryls, alkaryls and aralkyls such as phenyl, benzyl, tolyl, and cumyl; halogenated alkyls and aryls, such as chlorobutyl and chlorophenyl; and alkoxy aryls such as ethoxyphenyl and the like.

Especially preferred are such iodopropynyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

The algicides, that may be used in accordance with the present invention are well know and include, but are not limited to, those algicides selected from the group consisting of $N^2$-tert-butyl-$N^4$-ethyl-7-methylthio-1,3,5-triazine-2,4-diyldiamine, 2-methylthio-4-butylamino-6-cyclopropylamino-s-triazine, 4-butylamino-2-chloro-6-ethylamino-s-triazine, 2-t-butylamino-4-ethylamino-6-methoxy-s-triazine, 3-t-butyl-5-chloro-6-methyluracil, N'-(3,4-dichlorophenyl)-N,N-dimethylurea, 3-(4-isopropylphenyl)-1,1-dimethylurea and 2-chloro-4,6-bis (isopropylamino)-s-triazine.

Especially preferred are the algicides $N^2$-t-butyl-$N^4$-ethyl-7-methylthio-1,3,5-triazine-2,4-diyldiamine, 2-methylthio-4-t-butylamino-6-cyclopropylamino-s-triazine and N'-(3,4-dichlorophenyl)-N,N-dimethylurea.

While the addition of the algicide to the halopropynyl, BCM mixtures in any amounts will be beneficial in providing a broader spectrum antimicrobial, it is preferred to use an amount of algicide which is between 2% to 80% of the total antimicrobial mix with ranges of 4% to 60% being especially preferred.

In accordance with the invention, the combined antimicrobial constituents can be included in a final formulation for use in such end use applications as paints, coatings, EIFS, stucco, wood preservative coatings, adhesives, mineral slurries, leather finishes, wet blue hides, dispersions, emulsions, aqueous materials, optical brightners oil field chemicals, inks, caulking, sealants, textiles, and the like, in a broad range from about 0.004% to 2.0% active concentration. Such compositions can be prepared from highly concentrated compositions of the active ingredients by appropriate dilution. The optimum useful range is about 0.01% to 1.0% of combined active ingredients in the final formulations for such end use systems. With the use of such modified formulations in end use systems, it is possible to protect aqueous substrates for extended period of time against growth from microorganisms.

Compositions of the present invention will generally be formulated by mixing or dispersing the active ingredients in a selected proportion with a liquid vehicle for dissolving or suspending the active components. The vehicle may contain a diluent, an emulsifier and a wetting-agent. Expected uses of the biocidal compositions include the protection of paint, coatings, adhesives, aqueous industrial products, leather, wood products, inks, stucco, sealants, lubricants, caulkings, fresh sawn timber, and the like. The compositions of this invention may be provided as wettable powders; liquid mixtures such as dispersions, emulsions, microemulsions or in any other suitable product form which is desirable or most useful.

When preparing formulations of the present invention for specific applications, the composition also will likely be provided with adjuvants conventionally employed in compositions intended for such applications such as organic binding agents, additional fungicides, auxiliary solvents, processing additives, fixatives, plasticizers, UV-stabilizers or stability enhancers, water soluble or water insoluble dyes, color pigments, siccatives, corrosion inhibitors, antisettlement agents, anti-skinning agents and the like.

According to the present invention, substrates are protected from contamination by microorganisms simply by treating said substrate with a composition of the present invention. Such treating may involve mixing the composition with the substrate, coating or otherwise contacting the substrate with the composition and the like.

The following examples are presented to illustrate and explain the invention. Unless otherwise indicated, all references to parts and percentages are based on weight.

EXAMPLES

Example 1
Fungicidal Activity on Bovine Leather

Two compositions were evaluated with respect to the protection of wet blue leather using the test method described in ASTM D 4576-86 as modified below. Aspergillus niger ATCC 6275 was used as the microorganism and a malt agar (Difco # 0112) used as the growth medium. (The ASTM D 4576-86 test method was modified inasmuch as the leather was placed on the surface of the malt agar plates rather that being embedded in them.) The leather was exposed to fungicides for 15 hours in a tissue culture flask rotating machine operating at approximately 5 rpm. The weight of the water was 3 times the weight of the leather being treated ("300% float") and the dose of biocide was based on the wet weight of the leather.

The active ingredients tested were a composition of this invention having a ratio of about 3 parts BCM to 1 part IPBC and the industry standard TCMTB (2-thiocyanomethylthiobenzothiazole). The results of the tests presented in Table 1 are based on the average of 3 replicates and a rating system wherein 0 represents no growth on the leather sample, 1 indicates that between 0% and 2% of the surface is contaminated, 2 indicates that between 2% and 10% of the surface is contaminated, 3 indicates that between 10% and 20% of the surface is contaminated, 4 indicates that between 20% and 50% of the surface is contaminated and 5 indicates that between 50% and 100% of the surface is contaminated. The untreated control was rated 3.25. (Any value of 1 or higher indicates a test failure.)

TABLE 1

| % ACTIVE | 3:1 BCM:IPBC | TCMTB |
| --- | --- | --- |
| 0.05 | 0.00 | * |
| 0.10 | 0.00 | 1.25 |
| 0.15 | 0.00 | 1.00 |
| 0.20 | 0.00 | 0.00 |
| 0.25 | 0.00 | 0.00 |

*This sample was lost

These results clearly demonstrate that the BCM, IPBC combinations of this invention are very effective in this test for preventing fungal growth on wet blue leather and performed better than the industry standard, TCMTB.

Example 2
Fungicidal Activity on Goatskin

Wet-blue goatskin was treated with fungicides at a tannery in Mexico. Treatments were made by drumming the test fungicides with wet-blue leather. Fungicides used were dispersions of TCMTB (30% active), and a 3:1 BCM:IPBC mixture (50% active). All fungicides were diluted with water and dosed at the rates of 0.0, 0.025, 0.050, 0.075, 0.100, 0.125, and 0.150% based on the weight of the treated leather. Contact time was about 15 minutes. (All doses were made in terms of formulated product; not on the basis of active ingredient content.)

The treated wet-blue leather samples were returned to the Troy laboratory in Newark, N.J. and tested for resistance to attack according to the procedure described in ASTM D 4576-86 with Aspergillus niger (ATCC 6275) as the test fungus. Each test was replicated 3 times. Evaluations were made at 3, 7, and 18 days after inoculation. The data is set forth in tables 2 and 3 using the standard rating scale for the test method wherein 0 represents no growth, 1 indicates up to 25% of the surface is covered with fungus, 2 indicates that between 25% and 50% of the surface is covered with fungus, 3 indicates that between 50% and 75% of the surface is covered with fungus and 4 indicates that between 75% and 100% of the surface is covered with fungus. (Any value of 1 or higher indicates a test failure.)

TABLE 2

| | Dose of 3:1 BCM:IPBC Fungicide (50% active) | | | | | |
| --- | --- | --- | --- | --- | --- | --- |
| | 0.025 | 0.050 | 0.075 | 0.100 | 0.125 | 0.150 |
| Days | ASTM 4576-86 Test Results | | | | | |
| 3 | 4, 0, 0 | 0, 0, 0 | 0, 0, 0 | 0, 0, 0 | 0, 0, 0 | 0, 0, 0 |
| 7 | 4, 0, 0 | 0, 0, 0 | 0, 0, 4 | 0, 0, 0 | 0, 0, 0 | 0, 0, 0 |
| 18 | 4, 0, 0 | 0, 0, 0 | 0, 0, 4 | 0, 0, 0 | 0, 0, 0 | 0, 0, 0 |

TABLE 3

| | Dose of TCMTB Fungicide (30% active) | | | | | |
| --- | --- | --- | --- | --- | --- | --- |
| | 0.025 | 0.050 | 0.075 | 0.100 | 0.125 | 0.150 |
| Days | ASTM 4576-86 Test Results | | | | | |
| 3 | 4, 4, 0 | 4, 4, 4 | 4, 4, 4 | 4, 4, 4 | 4, 4, 4 | 4, 4, 4 |
| 7 | 4, 4, 0 | 4, 4, 4 | 4, 4, 4 | 4, 4, 4 | 4, 4, 4 | 4, 4, 4 |
| 18 | 4, 4, 0 | 4, 4, 4 | 4, 4, 4 | 4, 4, 4 | 4, 4, 4 | 4, 4, 4 |

In the 0.025% treatment it seems like one of the reps for TCMTB and BCM:IPBC may have been interchanged. The anomaly in one of the reps for BCM, IPBC at 0.075 is believed due to variations in uptake of fungicide by the hide.

In working with wet-blue hides, it was noticed that hides treated with BCM:IPBC mixture were softer and more flexible than hides treated with equivalent amounts of TMCTB This unexpected observation was also made by personnel working at the tannery in Mexico. This is a significant advantage for the BCM:IPBC mixture over TMCTB.

Example 3
Anti-sapstain Activity

A composition of this invention consisting of about 3 parts BCM to about 1 part IPBC was evaluated in an anti-sapstain test. In the test, small diameter (about 1 cm) eastern white pine (Pinus stobus) branches were harvested and cut into sections roughly 8 cm long. Sections were split longitudinally through the pith and dipped in the test products for 30 seconds. Levels tested were 0.025, 0.05, 0.10, 0.15, 0.20, 0.25, and 0.30% as actives. Samples were drained on a piece of filter paper for 2 minutes and then placed in plastic Petri dishes with a small amount of distilled water to maintain high relative humidity. Wood samples were held slightly above the surface of the water by small plastic supports. The treated samples of wood were then inoculated with a suspension of spores from the test fungus and incubated for 3 weeks at 27° C.

Test fungi were *Aspergillus niger* and *Ceratocystis pilifera*, both known to be involved with staining of fresh sawn lumber. Treatments that allowed development of any growth of fungus were failed. The results are reported in Table 4 as the minimum dose of fungicide that passed this test.

TABLE 4

Anti-Sapstain Test Results

| Fungicide Tested | Formulation | (% Actives Passing Test) |
|---|---|---|
| IPBC | Micro-emulsion | 0.2 |
| 3:1 BCM:IPBC | Emulsion | <0.025 |

The BCM, IPBC mixture is superior to the use of IPBC alone by a significant factor. (BCM alone is known to be ineffective in an anti-sapstain test.)

Example 4
Activity Against Alternaria

BCM, a commonly used fungicide, suffers from a weakness against alternaria which makes BCM less well suited for paints and coatings where activity against alternaria is important. This example shows that while one might expect the addition of IPBC to assist in the control of alternaria, the addition of small amounts of IPBC provide a higher level of protection than would be anticipated based on the expected additive effects. Furthermore the combinations of this invention, especially the preferred combinations, are shown to be effective for controlling alternaria.

The activity of the fungicide components in this test was determined by the following procedure known as the seeded agar test technique (S. S. Block, Disinfection, Sterilization, and Preservation 4th ed., pg 1070, Lea and Febiger, Philadelphia, 1991):

Blends of fungicides were prepared by combining Polyphase P100 and Mergal BCM in the various test ratios based on active ingredient content. These mixtures were prepared by weighing the individual components into a small beaker, and stirring them together into a homogeneous mixture. The following IPBC:BCM blends were prepared for evaluation: 1:2, 1:4, 1:8, 1:16 and 1:49. Each blend was run at the dose levels of 0.5, 1, 2, 4, 6, 8, 10, 20, 40, 60, 80, 100, 200, 400, 600, 800 and 1000 ppm. Positive controls of the pure fungicides were also run.

Nutrient medium (Difco #0112, Malt Extract Agar) for the test fungus was prepared according to directions provided by the manufacturer. The medium was autoclaved for sterility, and cooled to about 50° C. The test fungicide blends were weighed into the cooled nutrient medium, mixed by swirling, and poured into sterile plastic Petri plates to solidify. Each blend was replicated 3 times.

The medium was then inoculated with spore suspension prepared for actively growing cultures of *Alternaria alternate* (ATCC 20084) and incubated at 28° C. for 2 weeks. Growth of fungus anywhere on the plate was recorded as "+". Absence of fungus growth was recorded as "−". The minimum inhibitory concentration (MIC) was determined, i.e. the minimum concentration at which no growth occurred. These data are presented in Table 5.

The data was analyzed according to the procedure reported by F. C. Kull et.al in Applied Microbiology 9:538 (1961) wherein $Q_a$ and $Q_b$ are the MIC values for IPBC and BCM respectively, $Q_A$ and $Q_B$ represent the quantity of BCM and IPBC in each mixture producing the MIC endpoint, and the Synergistic Index (SI) is determined by the following equation.

$$Q_A/Q_a + Q_B/Q_b = SI$$

A value of SI <1 in the formula above indicates an activity greater than expected based on additivity, i.e. that synergism has occurred.

TABLE 5

| IPBC:BCM | | Results For the Various IPBC:BCM Blends Against *Alternaria alternata* | | | | | |
|---|---|---|---|---|---|---|---|
| Ratio | (W/W) | $Q_A$ | $Q_B$ | $Q_a$ | $Q_b$ | MIC (PPM) | SI |
| 1:2 | 33:67 | 0.66 | 1.34 | 0.5 | 1000 | 2 | 1.3 |
| 1:4 | 20:80 | 0.40 | 1.60 | 0.5 | 1000 | 2 | 0.8 |
| 1:8 | 11:89 | 0.44 | 3.56 | 0.5 | 1000 | 4 | 0.8 |
| 1:16 | 6:94 | 0.36 | 5.64 | 0.5 | 1000 | 6 | 0.7 |
| 1:49 | 2:98 | 0.20 | 9.80 | 0.5 | 1000 | 10 | 0.4 |

Example 5
Stability Tests

In this example a styrenated acrylic white house paint was used as the test medium to assess the tendency of IPBC to yellow in various BCM/IPBC-containing compositions. The composition of the paint is shown in Table 6.

TABLE 6

FORMULATION OF STYRENATED ACRYLIC WHITE HOUSE PAINT

| No | Ingredient | Supplier | % W/W |
|---|---|---|---|
| 1 | Water | | 9.30 |
| 2 | Tamol 850 (30%) | Rohm & Haas | 0.20 |
| 3 | Triton CF-10 | Union Carbide | 0.50 |
| 4 | KTPP | FMC | 0.50 |
| 5 | NH$_4$OH (7.0%) | | 0.20 |
| 6 | Collacral P:Water (1:1) | BASF | 3.00 |
| 7 | Mineral Spirits | | 1.20 |
| 8 | Texanol | Eastman | 0.80 |
| 9 | TiO$_2$ | Kerr-McGee | 15.00 |
| 10 | Camel White (CaCO$_3$) | Genstar | 26.00 |
| 11 | Nytal 300 | R. T. Vanderbilt | 6.40 |
| 12 | Nopco 8035 | Huls | 0.30 |
| 13 | Acronal 296D | BASF | 36.60 |
| | TOTAL | | 100.00 |

Dispersions were prepared, each containing blends of BCM (MERGAL BCM) and IPBC (Troysan Polyphase® P100) wherein the BCM:IPBC ratios were 1:1, 2:1, and 3:1. Each formulation was then incorporated into the white test paint by mixing in an amount sufficient to provide a test paint having a concentration of IPBC present at the levels indicated in Table 7 (0.1%, 0.15%, 0.2%, 0.30%). The mixtures were then allowed to stand overnight. The paint formulations containing the BCM/IPBC mixtures were then applied on a Leneta chart with help of a 3 mil Bird type applicator. The paint film was allowed to dry for 10–15 minutes and then sprayed with a clear non-yellowing varnish (~3 mils), namely, Kamar Varnish 1312. The varnish was obtained from Krylon Products Group, The Specialty Division, Division of Sherwin-Williams Company Ohio. The object of the varnish was to trap any of the chromophores formed during subsequent UV light exposure and to assure a short and reproducible test for accessing UV light-induced yellowing.

The charts were then exposed to 340 nm UV radiation for four hours in a Q UV cabinet. The yellowing was measured by Microflash 200D Color measurement device. The difference in yellowing, Δb, between a blank (the white test paint without fungicide) and the candidate paint sample was recorded and used as the response for each test The results are provided in Table 7.

TABLE 7

| % IPBC | IPBC | BCM:IPBC 1:1 | BCM:IPBC 2:1 | BCM:IPBC 3:1 |
|---|---|---|---|---|
| 0.1 | 1.22 | 0.98 | 0.56 | 0.42 |
| 0.15 | 1.79 | 1.97 | 1.53 | 0.92 |
| 0.20 | 1.95 | 2.54 | 2.41 | 1.30 |
| 0.30 | No Test | 3.16 | 3.15 | 2.37 |

A sample of the same paint was then kept at 40° C. in an oven for four weeks. This paint was then applied on a Leneta chart as described above and the UV test repeated. The results are provided in Table 8.

TABLE 8

| % IPBC | IPBC | BCM:IPBC 1:1 | BCM:IPBC 2:1 | BCM:IPBC 3:1 |
|---|---|---|---|---|
| 0.1 | 2.05 | 0.63 | 0.96 | 0.89 |
| 0.15 | 3.22 | 1.28 | 2.17 | 1.88 |
| 0.20 | 4.59 | 2.49 | 2.02 | 1.82 |
| 0.30 | No Test | 3.32 | 3.2 | 3.41 |

As the data clearly shows, the presence of BCM has a stabilizing effect on the IPBC and inhibits its tendency to yellow. (The control, IPBC alone, was not tested beyond the 0.2% concentration)

Example 6

Test Results in Paint

This example is provided to illustrate that the BCM,IPBC composition of this invention can be combined with other antimicrobials such as algicides to provide broader spectrum protection. In addition the following illustrates that optimization experiments using statistical methods also confirm that the optimum ratios, even when considering both fungicide and algicide performance, fall within the claimed ranges of the present invention.

In this example an acrylic, vinyl acrylic white house paint was used as the test medium. The composition of the paint is shown in Table 9.

TABLE 9

FORMULATION OF ACRYLIC, VINYL ACRYLIC WHITE HOUSE PAINT

| No | Ingredient | Supplier | % W/W |
|---|---|---|---|
| 1 | Natrosol 250 MHR 100% | Aqualon | 0.3 |
| 2 | Propylene glycol | | 1.7 |
| 3 | Tamol 850 (30%) | Rohm & Haas | 0.9 |
| 4 | KTPP | FMC | 0.12 |

TABLE 9-continued

FORMULATION OF ACRYLIC, VINYL ACRYLIC WHITE HOUSE PAINT

| No | Ingredient | Supplier | % W/W |
|---|---|---|---|
| 5 | Nopco NXZ | Hüls | 0.1 |
| 6 | Triton CF-10 | Union Carbide | 0.21 |
| 7 | Water | | 13.44 |
| 8 | Titanium dioxide | Kerr McGee | 14.5 |
| 9 | Minex 4 | Uniman | 15.7 |
| 10 | Silica (Silver Bond B) | Uniman | 6.4 |
| 11 | Attagel | Engelhard | 0.85 |
| 12 | UCAR 379 | Union Carbide | 6.31 |
| 13 | Rhoplex AC-264 (60.5%) | Rohm & Haas | 25.2 |
| 14 | Nopco NXZ | Hüls | 0.17 |
| 15 | Propylene glycol | | 4.1 |
| 16 | Natrosol 250 MHR(2.5%) | | 10.0 |
| | TOTAL | | 100.00 |

In the following tests, BCM and IPBC were used as the fungicides and $N^2$-butyl-$N^4$-ethyl-7-methylthio-1,3,5-triazine-2,4-diyldiamine, 2-methylthio-4-t-butylamino-6-cyclopropylamino-s-triazine and N'-(3,4-dichlorophenyl)-N,N-dimethylurea were used as the algicides. Mixture design was used in the optimization of the critical ingredients IPBC, BCM and the algicide. A level of 20% wt/wt of active ingredients was selected as the target. Mixtures evaluated were as shown in Table 10.

TABLE 10

| Test # | % Carb | % Poly | % Alg |
|---|---|---|---|
| 1 | 20.00 | 0.00 | 0.00 |
| 2 | 0.00 | 0.00 | 20.00 |
| 3 | 10.00 | 0.00 | 10.00 |
| 4 | 13.33 | 3.33 | 3.33 |
| 5 | 0.00 | 0.00 | 20.00 |
| 6 | 10.00 | 10.00 | 0.00 |
| 7 | 6.67 | 6.67 | 6.67 |
| 8 | 0.00 | 20.00 | 0.00 |
| 9 | 3.33 | 3.33 | 13.33 |
| 10 | 20.00 | 0.00 | 0.00 |
| 11 | 10.00 | 0.00 | 10.00 |
| 12 | 3.33 | 13.33 | 3.33 |
| 13 | 0.00 | 20.00 | 0.00 |
| 14 | 0.00 | 10.00 | 10.00 |
| 15 | 6.67 | 6.67 | 6.67 |

Test formulations of fungicides and algicides were prepared by weighing the appropriate amounts of actives and adding them to the test paint so that each test formulation was 20% actives and 80% paint. Each was stirred to achieve a homogeneous mixture. These test formulations were then incorporated into the test paint at the rate of 0.3% w/w, i.e. the final level of actives in the paint was 0.06%. The resulting paint-biocide mixtures were applied to filter paper using a standard 3 mil draw down bar to insure uniformity of the test paint film.

After drying for 48 hours at room temperature, the test paint was evaluated for fungicidal activity according to the test described in Federal Standard 141 (c) using a test inoculum composed of *Alternaria alternata* (ATCC 20084) plus Penicillium sp. (ATCC #12667). Inoculated test samples, on plates of malt agar (Difco #0112), were incubated for 28° C. for 3 weeks. Results were recorded as fungus units determined by comparison to a standard chart with a range of 1 to 15 fungus units. A value of 15 indicates the painted square was totally covered with fungus. Values 5 through 15 showed gradations of growth from very little fungus growing on the surface to the total coverage of 15. A rating of 4 shows growth on the edges of the test square only, 3 shows growth up to the edge but not growth on the surface, 2 shows growth up to the corners but not near the edges and 1 indicates no growth touching the test square.

In a separate test, algicidal activity was measured using an algicide test which is similar to the fungicide test but adapted to the growth requirements of algae. The inoculum contained a mixture of algae consisting of *Stichococcus bacillaris* (CCAP #379/A)and *Chlorella vulgaris* (ATCC #16487) cultures in roughly a 50:50 ratio. Growth medium for algae tests was soil extract agar. Incubation time was three weeks at 17° C. and light intensity of 4000 Lux. The algae incubator was maintained at 52% relative humidity. In examples 6B and 6C the results were reported in terms of the width (mm) of the zone of inhibition surrounding the test paint. In example 6A the results were reported by measuring growth on the paint using a rating system wherein 0 represents no growth, 1 indicates a trace of growth (<1%), 2 indicates growth on from about 10% to 20% of the surface, 3 indicates growth on from about 20% to 40% of the paint surface, 4 indicates that between 40% and 80% of the surface is covered and 5 indicates that between 80% and 100% of the surface is covered.

The experimental design consisted of three independent variables at three levels. Some of the points were duplicated so as to evaluate experimental error using internal replication. In total, 15 trials were required (Table 10).

The range used for the independent variables was 0 to 20% wt/wt active ingredient. These ranges were selected to insure evaluation of the effects over the widest possible range within the constraint that the total active level for all ingredients was limited to 20% w/w.

All statistical procedures are described by Snee (Design and Analysis of Mixture Experiments, J. Of Quality Technology, Vol 3, No. 4, October 1971). Polynomial mixture models were used to predict the responses of the dependent variables to changes in the concentrations of fungicides and algicides. Tables 12, 13 and 14 show the whole set of experiments with results for fungicidal and algicidal activity of the dry paint film for the three algicides respectively.

Statistical analysis shows a statistically significant and highly reliable fit for the data in all there tables. Correlation coefficients for the models were 85±1 for the fungi and 85±10 for the algae. (Such statistical details are described in Steel and Torrie, Principles and Procedures of Statistics, McGraw-Hill, 1960.

TABLE 12

EXAMPLE 6A - N'-(3,4-DICHLOROPHENYL)-N,N-DIMETHYLUREA USED AS ALGICIDE

| Test# | % Carb | % IPBC | % Alg | Fungus | Algae |
|---|---|---|---|---|---|
| 1 | 20.00 | 0.00 | 0.00 | 11 | 5.00 |
| 2 | 0.00 | 0.00 | 20.00 | 15 | 0.00 |
| 3 | 10.00 | 0.00 | 10.00 | 15 | 1.00 |
| 4 | 13.33 | 3.33 | 3.33 | 1 | 1.00 |
| 5 | 0.00 | 0.00 | 20.00 | 15 | 0.00 |
| 6 | 10.00 | 10.00 | 0.00 | 1 | 5.00 |
| 7 | 6.67 | 6.67 | 6.67 | 1 | 1.00 |
| 8 | 0.00 | 20.00 | 0.00 | 1 | 5.00 |
| 9 | 3.33 | 3.33 | 13.33 | 1 | 1.00 |
| 10 | 20.00 | 0.00 | 0.00 | 12 | 5.00 |
| 11 | 10.00 | 0.00 | 10.00 | 15 | 1.00 |
| 12 | 3.33 | 13.33 | 3.33 | 1 | 0.00 |
| 13 | 0.00 | 20.00 | 0.00 | 1 | 5.00 |

TABLE 12-continued

EXAMPLE 6A - N'-(3,4-DICHLOROPHENYL)-N,N-DIMETHYLUREA USED AS ALGICIDE

| Test# | % Carb | % IPBC | % Alg | Fungus | Algae |
|---|---|---|---|---|---|
| 14 | 0.00 | 10.00 | 10.00 | 1 | 1.00 |
| 15 | 6.67 | 6.67 | 6.67 | 1 | 3.00 |

In this example, the best results against both fungi and algae would be obtained with a formulation that was 14.94% BCM, 4.02% IPBC and 1.04% algicide.

TABLE 13

EXAMPLE 6B - 2-METHYLTHIO-4-TERTIARYBUTYLAMINO-6-CYCLO-PROPYLAMINO-S-TRIAZINE USED AS ALGICIDE

| Test# | % Carb | % IPBC | % Alg | Fungus | Algae |
|---|---|---|---|---|---|
| 1 | 20.00 | 0.00 | 0.00 | 15 | 0.00 |
| 2 | 0.00 | 0.00 | 20.00 | 15 | 30.33 |
| 3 | 10.00 | 0.00 | 10.00 | 15 | 23.67 |
| 4 | 13.33 | 3.33 | 3.33 | 13 | 21.67 |
| 5 | 0.00 | 0.00 | 20.00 | 15 | 28.33 |
| 6 | 10.00 | 10.00 | 0.00 | 6 | 0.00 |
| 7 | 6.67 | 6.67 | 6.67 | 5.33 | 20.67 |
| 8 | 0.00 | 20.00 | 0.00 | 4.33 | 0.00 |
| 9 | 3.33 | 3.33 | 13.33 | 13 | 27.33 |
| 10 | 20.00 | 0.00 | 0.00 | 15 | 10.33 |
| 11 | 10.00 | 0.00 | 10.00 | 15 | 24.33 |
| 12 | 3.33 | 13.33 | 3.33 | 4.33 | 12.67 |
| 13 | 0.00 | 20.00 | 0.00 | 2 | 0.00 |
| 14 | 0.00 | 10.00 | 10.00 | 3 | 25.00 |
| 15 | 6.67 | 6.67 | 6.67 | 8.67 | 20.00 |

In this example the best results against both fungi and algae would be obtained with a formulation that was 6.80% BCM, 2.01% IPBC and 11.19% algicide.

TABLE 14

EXAMPLE 6C - N²-TERTIARYBUTYL-N⁴-ETHYL-7-METHYLTHIO-1,3,5-TRIAZINE-2,4-DIYLDIAMINE USED AS ALGICIDE

| Test | % Carb | % IPBC | % Alg | Fungus | Algae |
|---|---|---|---|---|---|
| 1 | 20.00 | 0.00 | 0.00 | 15 | 0.00 |
| 2 | 0.00 | 0.00 | 20.00 | 15 | 46.00 |
| 3 | 10.00 | 0.00 | 10.00 | 15 | 46.00 |
| 4 | 13.33 | 3.33 | 3.33 | 1 | 25.00 |
| 5 | 0.00 | 0.00 | 20.00 | 15 | 46.00 |
| 6 | 10.00 | 10.00 | 0.00 | 1 | 0.00 |
| 7 | 6.67 | 6.67 | 6.67 | 1 | 25.00 |
| 8 | 0.00 | 20.00 | 0.00 | 1 | 0.00 |
| 9 | 3.33 | 3.33 | 13.33 | 1 | 46.00 |
| 10 | 20.00 | 0.00 | 0.00 | 15 | 0.00 |
| 11 | 10.00 | 0.00 | 10.00 | 15 | 46.00 |
| 12 | 3.33 | 13.33 | 3.33 | 1 | 25.00 |
| 13 | 0.00 | 20.00 | 0.00 | 1 | 0.00 |
| 14 | 0.00 | 10.00 | 10.00 | 1 | 28.60 |
| 15 | 6.67 | 6.67 | 6.67 | 1 | 25.00 |

In this example, the best results against both fungi and algae would be obtained with a formulation that was 11.51% BCM, 4.45% IPBC and 4.04% algicide.

The data shows that with three different algicides, the most efficient combinations fall within the claims of this invention.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

What is claimed is:

1. An antimicrobial composition comprising synergistic effective amounts of 3-iodo-2-propynyl butyl carbamate and 2-(methoxycarbonylamino)benzimidazole, wherein the 3-iodo-2-propynyl butyl carbamate and the 2-(methoxycarbonylamino)benzimidazole are present in a proportion of from about 100 parts 2-(methoxycarbonylamino)benzimidazole to one part 3-iodo-2-propynyl butyl carbamate to greater than two parts 2-(methoxycarbonylamino)benzimidazole to about one part 3-iodo-2-propynyl butyl carbamate.

2. The composition of claim 1 wherein the 3-iodo-2-propynyl butyl carbamate and the 2-(methoxycarbonylamino)benzimidazole are present in a proportion of from about six parts 2-(methoxycarbonylamino)benzimidazole to one part of the 3-iodo-2-propynyl butyl carbamate to greater than two parts 2-(methoxycarbonylamino)benzimidazole to about one part of the 3-iodo-2-propynyl butyl carbamate.

3. The composition of claim 2 wherein the 3-iodo-2-propynyl butyl carbamate and the 2-(methoxycarbonylamino)benzimidazole are present in a proportion of from about four parts 2-(methoxycarbonylamino)benzimidazole to one part 3-iodo-2-propynyl butyl carbamate to greater than two parts 2-(methoxycarbonylamino)benzimidazole to about one part 3-iodo-2-propynyl butyl carbamate.

4. The composition of claim 3 wherein the 3-iodo-2-propynyl butyl carbamate and the 2-(methoxycarbonylamino)benzimidazole are present in a ratio of about three to four parts of 2-(methoxycarbonylamino)benzimidazole to one part 3-iodo-2-propynyl butyl carbamate.

5. An antimicrobial composition comprising: synergistic effective amounts of a) 3-iodo-2-propynyl butyl carbamate, b) 2-(methoxycarbonylamino)benzimidazole and c) an algicide selected from the group consisting of $N^2$-t-butyl-$N^4$-ethyl-7-methylthio-1,3,5-triazine-2,4-diyldiamine, 2-methylthio-4-tert-butylamino-6-cyclopropyl-amino-s-triazine, 4-t-butylamino-2-chloro-6-ethylamino-s-triazine, 2-t-butylamino-4-ethylamino-6-methoxy-s-triazine, 3-t-butyl-5-chloro-6-methyluracil, N'-(3,4-dichlorophenyl)-N,N-dimethylurea, 3-(4-isopropylphenyl)-1,1-dimethylurea and 2-chloro-4,6-bis(isopropylamino)-s-triazine wherein the ratio of 2-(methoxycarbonylamino) benzimidazole to the 3-iodo-2-propynyl butyl carbamate is from about 20:1 to greater than 2:1.

6. The composition of claim 5 wherein the algicide is chosen from the group consisting of $N^2$-t-butyl-$N^4$-ethyl-7-methylthio-1,3,5-triazine-2,4-diyldiamine, 2-methylthio-4-t-butylamino-6-cyclopropylamino-s-triazine and N'-(3,4-dichlorophenyl)-N,N-dimethylurea.

7. The composition of claim 6 wherein the algicide is from about 4% to about 60% of the antimicrobial mixture.

8. The composition of claim 7 wherein the 3-iodo-2-propynyl butyl carbamate and the 2-(methoxycarbonylamino)benzimidazole are present in a ratio of about three to four parts of 2-(methoxycarbonylamino)benzimidazole to one part 3-iodo-2-propynyl butyl carbamate.

9. A paint containing an antimicrobial composition comprising synergistic effective amounts of 3-iodo-2-propynyl butyl carbamate and 2-(methoxycarbonylamino)benzimidazole wherein the 3-iodo-2-propynyl butyl carbamate and 2-(methoxycarbonylamino)benzimidazole are present in a proportion of from about six parts 2-(methoxycarbonylamino)benzimidazole to one part of the 3-iodo-2-propynyl butyl carbamate to greater than two parts 2-(methoxycarbonylamino)benzimidazole to about one part of the 3-iodo-2-propynyl butyl carbamate.

10. The paint of claim 9 wherein the 3-iodo-2-propynyl butyl carbamate and the 2-(methoxycarbonylamino) benzimidazole are present in a proportion of from about four parts 2-(methoxycarbonylamino)benzimidazole to one part of the iodopropynyl compound to greater than two parts 2-(methoxycarbonylamino)benzimidazole to about one part of the 3-iodo-2-propynyl butyl carbamate.

11. The paint of claim 10 wherein the 3-iodo-2-propynyl butyl carbamate and the 2-(methoxycarbonylamino) benzimidazole are present in a ratio of about three to four parts of 2-(methoxycarbonylamino)benzimidazole to one part 3-iodo-2-propynyl butyl carbamate.

12. A paint containing the antimicrobial composition comprising synergistic effective amounts of 3-iodo-2-propynyl butyl carbamate, 2-methoxycarbonylamino)benzimidazole and an algicide chosen from the group consisting of $N^2$-t-butyl-$N^4$-ethyl-7-methylthio-1,3,5-triazine-2, 4-diyldiamine, 2-methylthio-4-t-butylamino-6-cyclopropylamino-s-triazine and N'-(3,4-dichlorophenyl)-N,N-dimethylurea wherein the 3-iodo-2-propynyl butyl carbamate and 2-(methoxycarbonylamino)benzimidazole are present in a proportion of from about six parts 2-(methoxycarbonylamino)benzimidazole to one part of the 3-iodo-2-propynyl butyl carbamate to greater than two parts 2-(methoxycarbonylamino)benzimidazole to about one part of the 3-iodo-2-propynyl butyl carbamate.

13. The paint of claim 12 wherein the algicide is from about 4% to about 60% of the antimicrobial mixture.

14. A method for protecting wet blue leather from fungal infestation which comprises treating said leather with an antimicrobial composition comprising synergistic effective amounts of 3-iodo-2-propynyl butyl carbamate and 2-(methoxycarbonylamino)benzimidazole wherein the 3-iodo-2-propynyl butyl carbamate and the 2-(methoxycarbonylamino)benzimidazole are present in a proportion of from about six parts 2-(methoxycarbonylamino)benzimidazole to one part of the 3-iodo-2-propynyl butyl carbamate to greater than two parts 2-(methoxycarbonylamino)benzimidazole to one part of the 3-iodo-2-propynyl butyl carbamate.

15. The method of claim 14 wherein the 3-iodo-2-propynyl butyl carbamate and the 2-(methoxycarbonylamino)benzimidazole are present in a proportion of from about four parts 2-(methoxycarbonylamino)benzimidazole to one part of the 3-iodo-2-propynyl butyl carbamate to greater than two parts 2-(methoxycarbonylamino)benzimidazole to one part of the 3-iodo-2-propynyl butyl carbamate.

16. The method of claim 15 wherein the 3-iodo-2-propynyl butyl carbamate and the 2-(methoxycarbonylamino)benzimidazole are present in a ratio of about three to four parts of 2-(methoxycarbonylamino)benzimidazole to one part 3-iodo-2-propynyl butyl carbamate.

17. A method for protection of fresh cut timber from sapstain which comprises treating said timber with an antimicrobial composition comprising synergistic effective amounts of 3-iodo-2-propynyl butyl carbamate and 2-(methoxycarbonylamino)benzimidazole wherein the 3-iodo-2-propynyl butyl carbamate and the 2-(methoxycarbonylamino)benzimidazole are present in a proportion of from about six parts 2-(methoxycarbonylamino)benzimidazole to one part of the 3-iodo-2-propynyl butyl carbamate to greater than two parts 2-(methoxycarbonylamino)benzimidazole to about one part of the 3-iodo-2-propynyl butyl carbamate.

18. The method of claim 17 wherein the 3-iodo-2-propynyl butyl carbamate and the 2-(methoxycarbonylamino)benzimidazole are present in a proportion of from about four parts 2-(methoxycarbonylamino)benzimidazole to one part of the 3-iodo-2-propynyl butyl carbamate to greater than two parts 2-(methoxycarbonylamino)benzimidazole to about one part of the 3-iodo-2-propynyl butyl carbamate.

19. The method of claim 18 wherein the 3-iodo-2-propynyl butyl carbamate and the 2-(methoxycarbonylamino)benzimidazole are present in a ratio of about three to four parts 2-(methoxycarbonylamino)benzimidazole to one part 3-iodo-2-propynyl butyl carbamate.

* * * * *